United States Patent
Schuetzle et al.

(10) Patent No.: US 12,103,897 B2
(45) Date of Patent: *Oct. 1, 2024

(54) PROCESS FOR CONVERSION OF CARBON DIOXIDE AND POWER INTO FUELS AND CHEMICALS

(71) Applicant: INFINIUM TECHNOLOGY, LLC, Sacramento, CA (US)

(72) Inventors: Robert Schuetzle, Sacramento, CA (US); Dennis Schuetzle, Grass Valley, CA (US); Harold Wright, Menomonee Falls, WI (US); Orion Hanbury, Sacramento, CA (US); Matthew Caldwell, West Sacramento, CA (US); Ramer Rodriguez, Sacramento, CA (US)

(73) Assignee: Infinium Technology, LLC, Sacramento, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/803,830

(22) Filed: Dec. 13, 2022

(65) Prior Publication Data

US 2023/0159408 A1    May 25, 2023

Related U.S. Application Data

(63) Continuation of application No. 17/300,262, filed on May 3, 2021, now Pat. No. 11,565,982.

(Continued)

(51) Int. Cl.
*C07C 1/04* (2006.01)
*C01B 3/40* (2006.01)
(Continued)

(52) U.S. Cl.
CPC .............. *C07C 1/0485* (2013.01); *C01B 3/40* (2013.01); *C01B 32/40* (2017.08); *C25B 1/04* (2013.01);
(Continued)

(58) Field of Classification Search
CPC .... C07C 1/0485; C10G 2/32; C10G 2400/20; C01B 2203/0244; C01B 2203/1241;
(Continued)

(56) References Cited

U.S. PATENT DOCUMENTS 7,485,767 B2    2/2009   Lattner et al.
8,168,143 B2    5/2012   Severinsky
(Continued)

FOREIGN PATENT DOCUMENTS

WO       03035590 A1    5/2003
WO    2008153826 A2   12/2008

OTHER PUBLICATIONS

Albrecht. F, Prospects of electrofuels to defossilize transportation in Denmark—A techno-economic and ecological analysis, Energy 192 (2020) 116511.
Kibby, C. Chevron's gas conversion catalysis-hybrid catalysts for wax-free Fischer-Tropsch synthesis, Catalysis Today 215 (2013) 131-141.
Diamond, Alan, Office Action in United States Ex Parte Reexamination for U.S. Pat. No. 11565982, dated May 21, 2024, 28 pages.

*Primary Examiner* — Jafar F Parsa
(74) *Attorney, Agent, or Firm* — McKinney Law Group APC; Jeffrey A. McKinney

(57) ABSTRACT

The present invention describes a processes, systems, and catalysts for the conversion of carbon dioxide and water and electricity into low carbon or zero carbon high quality fuels and chemicals. In one aspect, the present invention provides an integrated process for the conversion of a feed stream comprising carbon dioxide to a product stream comprising hydrocarbons between 5 and 24 carbon atoms in length.

19 Claims, 3 Drawing Sheets

Related U.S. Application Data

(60) Provisional application No. 63/101,556, filed on May 4, 2020.

(51) Int. Cl.
    *C01B 32/40*     (2017.01)
    *C25B 1/04*     (2021.01)
    *C25B 15/08*     (2006.01)

(52) U.S. Cl.
    CPC .... *C25B 15/081* (2021.01); *C01B 2203/0233* (2013.01); *C01B 2203/0244* (2013.01); *C01B 2203/1241* (2013.01)

(58) Field of Classification Search
    CPC ............ C01B 2203/0233; C01B 32/40; C01B 3/40; C25B 1/04; C25B 15/081
    See application file for complete search history.

(56) References Cited

U.S. PATENT DOCUMENTS

| | | |
|---|---|---|
| 8,198,338 B2 | 6/2012 | Schulenberger et al. |
| 11,565,982 B2 | 1/2023 | Schuetzle et al. |
| 11,649,164 B2 | 5/2023 | Mortensen |
| 11,655,421 B2 * | 5/2023 | Heidel ............ C10L 1/04 518/703 |
| 2007/0244208 A1 | 10/2007 | Shulenberger et al. |
| 2009/0012188 A1 | 1/2009 | Rojey et al. |
| 2010/0298131 A1 | 11/2010 | Ni et al. |
| 2012/0201717 A1 | 8/2012 | Singh et al. |
| 2016/0199810 A1 | 7/2016 | Goeppert et al. |
| 2016/0186069 A1 | 8/2016 | Bashir et al. |
| 2018/0093888 A1 | 4/2018 | Mamedov et al. |
| 2021/0113980 A1 | 4/2021 | Van Der Ploeg |

\* cited by examiner

PROCESS FOR CONVERSION OF CARBON DIOXIDE AND POWER INTO FUELS AND CHEMICALS

This application is a continuation of U.S. application Ser. No. 17/300,262, filed on May 3, 2021, which claims priority benefit of U.S. Provisional Patent Application No. 63/101,556, filed May 4, 2020. The entire content of these applications is hereby incorporated by reference herein in its entirety.

FIELD OF THE INVENTION

The present invention describes a catalytic process for the conversion of carbon dioxide and water and electricity, ideally renewable or low carbon electricity, into low carbon or zero carbon high quality fuels and chemicals. Process conversion efficiency is enhanced by incorporating several innovative processes that have not been described in the current art. The first improvement is an autothermal reforming (ATR) process that converts the tail gas (and potentially other hydrocarbon feedstocks) from the fuel/chemical production stage and oxygen from the electrolysis processes into additional syngas. The second improvement is the use of heat energy from the ATR process for operation of the (CO2) RWGS (hydrogenation) catalyst. The third enhancement is the separation and conversion of the CO2 from the ATR process into additional syngas using the CO2 hydrogenation catalyst. The fourth is using a unique Reverse Water Gas Shift (RWGS) catalyst, reactor, and process for converting CO2 and Hydrogen into syngas and preferably operating this RWGS operation at a pressure that is close to the pressure of the fuel/chemical production process, which converts the syngas into fuels or chemicals. Most preferably these fuels or chemicals are paraffinic or olefinic hydrocarbon liquids with a majority being in the C5-C24 range.

BACKGROUND OF THE INVENTION

Carbon dioxide is produced by many industrial and biological processes. Carbon dioxide is usually discharged into the atmosphere. However, since carbon dioxide has been identified as a significant greenhouse gas, these carbon dioxide emissions need to be reduced from these processes. Although, this carbon dioxide can be used to enhance oil and gas recovery from wells in limited cases, most of this captured carbon dioxide will be emitted into the atmosphere. A preferred method to deal with carbon dioxide is to efficiently capture and utilize the carbon dioxide and convert it into useful products such as fuels (e.g. diesel fuel, gasoline, gasoline blendstocks, jet fuel, kerosene, other) and chemicals (e.g. solvents, olefins, alcohols, aromatics, lubes, waxes, ammonia, methanol, other) that can displace fuels and chemicals produced from fossil sources such as petroleum and natural gas and therefore lower the total net emissions of carbon dioxide into the atmosphere. This is what is meant by low carbon, very low carbon, or zero carbon fuels and chemicals.

Carbon dioxide can be obtained from several sources. Industrial manufacturing plants that produce ammonia for fertilizer produce large amounts of carbon dioxide. Ethanol plants that convert corn or wheat into ethanol produce large amounts of carbon dioxide. Power plants that generate electricity from various resources (for example natural gas, coal, other resources) produce large amounts of carbon dioxide. Chemical plants such as nylon production plants, ethylene production plants, other chemical plants produce large amounts of carbon dioxide. Some natural gas processing plants produce $CO_2$ as part of the process of purifying the natural gas to meet pipeline specifications. Capturing $CO_2$ for utilization as described here often involves separating the carbon dioxide from a flue gas stream or another stream where the carbon dioxide is not the major component. Some $CO_2$ sources are already relatively pure and can be used with only minor treatment (which may include gas compression) in the processes described herein. Some processes may require an alkylamine or other method that would be used to remove the carbon dioxide from the flue gas steam. Alkylamines used in the process include monoethanolamine, diethanolamine, methydiethanolamine, disopropylamine, aminoethoxyethnol, or combinations thereof. Metal Organic Framework (MOF) materials have also been used as a means of separating carbon dioxide from a dilute stream using chemisorption or physisorption to capture the carbon dioxide from the stream. Other methods to get concentrated carbon dioxide include chemical looping combustion where a circulating metal oxide material captures the carbon dioxide produced during the combustion process. Carbon dioxide can also be captured from the atmosphere in what is called direct air capture (DAC) of carbon dioxide.

Renewable sources of Hydrogen ($H_2$) can be produced from water via electrolysis.

$$H_2O = H_2 + \frac{1}{2}O_2$$

This reaction uses electricity to split water into hydrogen and oxygen. Electrolyzers consist of an anode and a cathode separated by an electrolyte. Different electrolyzers function in slightly different ways, mainly due to the different type of electrolyte material involved.

However, each electrolysis technology has a theoretical minimum electrical energy input of 39.4 kWh/kgH$_2$ (HHV of hydrogen) if water is fed at ambient pressure and temperature to the system and all energy input is provided in the form of electricity. The required electrical energy input may be reduced below 39.4 kWh/kgH$_2$ if suitable heat energy is provided to the system. Besides electrolysis, significant current research is examining ways to split water into hydrogen and oxygen using light energy and a photocatalyst. (Acar et al, *Int. J. Energy Res.* 2016; 40:1449-1473).

One reaction that has been considered for utilization of carbon dioxide is the Reverse Water Gas Shift (RWGS) reaction.

$$CO_2 + H_2 = CO + H_2O$$

This reaction converts carbon dioxide and hydrogen to carbon monoxide and water. This reaction is endothermic at room temperature and requires heat to proceed and elevated temperature and a good catalyst is required for significant carbon dioxide conversion. A number of catalysts have been disclosed for the RWGS reaction. The primary catalyst studied previously were Cu or Pt or Rh dispersed on metal oxide supports. (Daza & Kuhn, RSC Adv. 2016, 6, 49675-49691).

With the CO (Carbon Monoxide) from the Reverse Water Gas Shift reaction and hydrogen from the electrolysis of water, the potential exists for useful products through the catalyst hydrogenation of carbon monoxide to hydrocarbons. Mixtures of $H_2$ and CO are called synthesis gas or syngas. Syngas may be used as a feedstock for producing a wide range of chemical products, including liquid fuels, alcohols, acetic acid, dimethyl ether, methanol, ammonia, and many other chemical products.

The catalytic hydrogenation of carbon monoxide to produce light gases, liquids and waxes, ranging from methane to heavy hydrocarbons (C100 and higher) in addition to oxygenated hydrocarbons, is typically referred to Fischer-Tropsch (or F-T) synthesis. Traditional low temperature (<250° C.) F-T processes primarily produce a high weight (or wt. %) F-T wax (C25 and higher) from the catalytic conversion process. These F-T waxes are then hydrocracked and/or further processed to produce, diesel, naphtha, and other fractions. During this hydrocracking process, light hydrocarbons are also produced, which may require additional upgrading to produce viable products. The catalysts that are commonly used for F-T are either Cobalt (Co) based, or Iron (Fe) based catalysts are also active for the water gas shift (WGS) reaction that results in the conversion of feed carbon monoxide to carbon dioxide. See more details about the state of the art in Fischer-Tropsch (S. S. Ail, S. Dasappa/ Renewable and Sustainable Energy Reviews 58 (2016) 267-286).

To date, efficient and economical processes, systems, and catalysts to convert carbon dioxide to useful fuels and chemicals have not been developed. There is a need for better processes, systems, and catalysts.

BRIEF DESCRIPTION OF THE FIGURES

FIG. 1 shows a part of an overall process flow diagram for the conversion of $H_2$ and $CO_2$ to fuels and chemicals. Specifically, FIG. 1 the reverse water gas shift reactor system to produce CO from $CO_2$.

FIG. 2 shows a part of an overall process flow diagram for the conversion of $H_2$ and $CO_2$ to fuels and chemicals. Specifically, FIG. 2 shows the liquid fuel production system where CO and $H_2$ are reacted to produce longer chain hydrocarbons that can be used as fuel or chemicals as well as the ATR for tailgas conversion.

FIG. 3 shows a part of an overall process flow diagram for the conversion of $H_2$ and $CO_2$ to fuels and chemicals. Specifically, FIG. 3 shows the electrolysis unit to produce hydrogen and oxygen from water and low carbon power.

SUMMARY OF THE INVENTION

The invention relates to a process to convert carbon dioxide, water, and electricity to useful chemicals and fuels. The process involves conversion of water to hydrogen in an efficient electrolysis unit that uses electricity, ideally renewable electricity, as its energy source. Carbon dioxide and hydrogen are reacted to carbon monoxide and water in a Reverse Water Gas Shift (RWGS) reactor where the heat of reaction is provided by renewable electricity. The catalyst used in the reactor is a novel solid solution catalyst. The product carbon monoxide and additional hydrogen are reacted to fuels and chemicals in a liquid fuels production reactor that uses a novel catalyst to directly produce fuels and chemicals. Various fuels or chemicals can be produced from syngas as described herein. Preferably, the product produced is a hydrocarbon with 4 to 24 carbon atoms in length. Process conversion efficiency is enhanced, and capital cost is reduced, by incorporating several innovative operations into the process. The first improvement is an autothermal reforming (ATR) process that converts the tail gas (and potentially other hydrocarbon feedstocks) from the fuel/chemical production process and oxygen from the electrolysis processes into additional syngas. The second improvement is the use of heat energy from the ATR process for operation of the CO2 hydrogenation catalyst. The third enhancement is the conversion of the CO2 from the ATR process into additional syngas using the CO2 hydrogenation catalyst. The fourth is using a unique Reverse Water Gas Shift (RWGS) catalyst and process for converting CO2 and Hydrogen into syngas and preferably operating this RWGS operation at a pressure that is close to the pressure of the fuel/chemical production process, which preferably converts the syngas into hydrocarbon liquids with a majority being in the C5-C24 range.

DETAILED DESCRIPTION OF THE INVENTION

Figure 1:
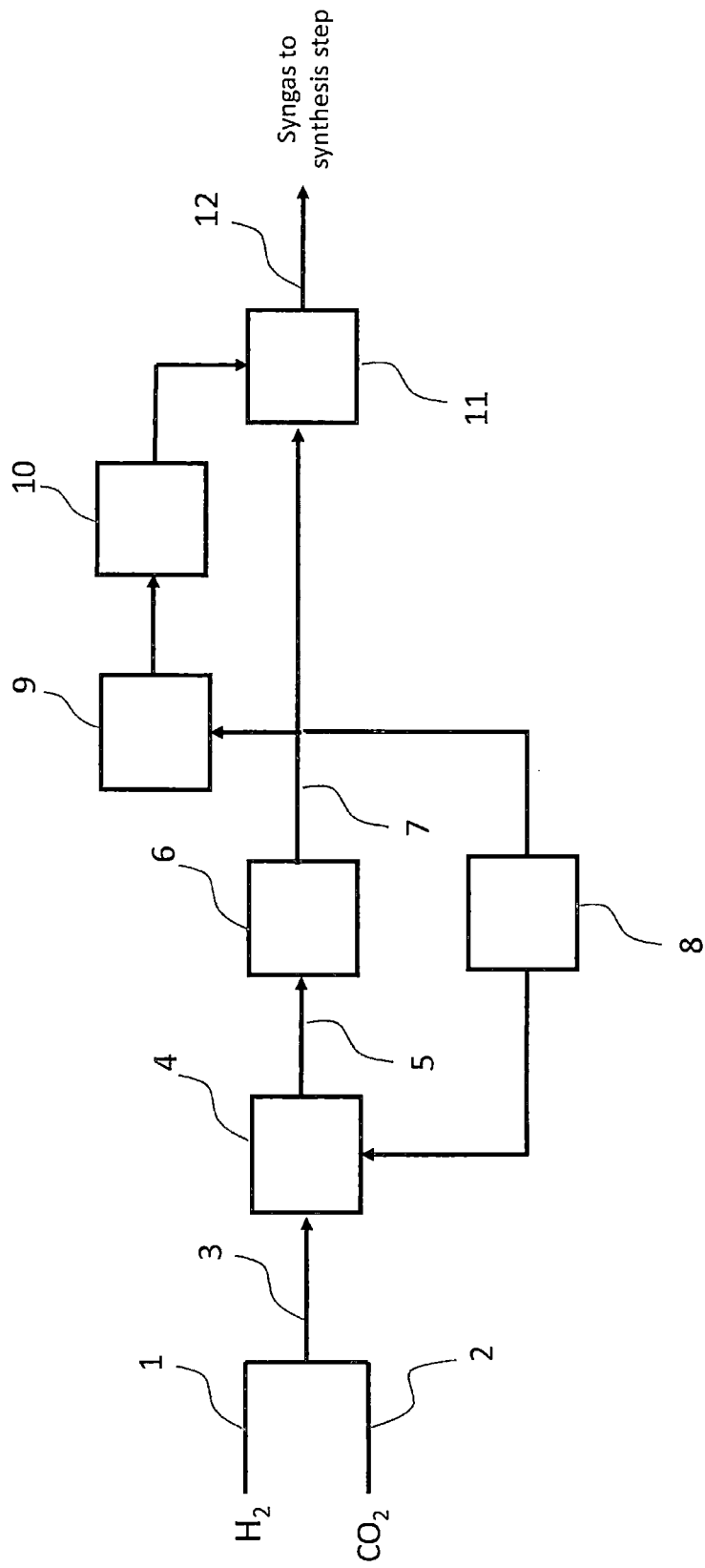
FIGS. 1-3 show an integrated high efficiency process for the conversion of carbon dioxide, water, and renewable electricity into renewable fuels and chemicals.

FIG. 1 shows several subsystems 1) the electrolysis system to produce hydrogen from water, 2) the reverse water gas shift reactor (RWGS) system to produce CO from $CO_2$, 3) the auto thermal reformer (ATR) section, 4) the syngas compression system.

Water is fed to the electrolysis system. Renewable electricity is used to power the electrolysis system. Hydrogen can be produced by electrolysis of water.

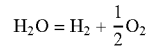

Electrolyzers consist of an anode and a cathode separated by an electrolyte. Different electrolysers function in slightly different ways. Different electrolyzer designs that use different electrolysis technology can be used including alkaline electrolysis, membrane electrolysis, and high temperature electrolysis. Alkaline electrolysis is preferred as it is commercially capable of the larger >1 MW scale operation. Different electrolytes can be used including liquids KOH and NaOH with or without activating compounds can be used. Activating compounds can be added to the electrolyte to improve the stability of the electrolyte. Most ionic activators for hydrogen evolution reaction are composed of ethylenediamine (en)-based metal chloride complex ([M(en)3]Clx,M ¼Co, Ni, et al.) and $Na_2MoO_4$ or $Na_2WO_4$. Different electrocatalysts can be used on the electrodes including many different combinations of metals and oxides like Raney-Nickel-Aluminum, which can be enhanced by adding cobalt or molybdenum to the alloy. Several combinations of transition metals, such as $Pt_2Mo$, $Hf_2Fe$, and TiPt, have been used as cathode materials and have shown significantly higher electrocatalytic activity than state-of-the-art electrodes.

Water at the cathode combines with electrons from the external circuit to form hydrogen gas and negatively charged oxygen ions. The oxygen ions pass through the solid ceramic membrane and react at the anode to form oxygen gas and generate electrons for the external circuit. In this way, both hydrogen gas and oxygen gas are produced in the electrolyzer. In one embodiment, multiple electrolysers are operated in parallel. No electrolyzer operates with 100% energy efficiency and energy usage is critical to the economic operation of the facility. The energy usage in the electrolyzer should be less than 200 mega-watthours (MWh)/metric ton (MT) of $H_2$ produced, and preferably less than 120 MWh/ MT $H_2$ produced and more preferably less than 60 MWh/MT $H_2$ produced. For the alkaline electrolyzer embodiment, the electricity usage will be greater than 39.4 MWh/MT $H_2$ produced. However, for the high temperature electrolyzer embodiment, the electricity usage can potentially be less than 39.4 MWh/MT $H_2$ produced if waste heat is used to heat the electrolyzer above ambient temperature.

Carbon dioxide can come from numerous industrial and natural sources. Carbon dioxide is often found in natural gas deposits. Carbon dioxide is emitted from many biological processes such as anaerobic digestion. Many other processes (e.g., power plants, cement plants, ethanol production, petroleum refining, chemical plants, etc.) produce carbon dioxide which is usually discharged into the atmosphere. Carbon dioxide can also be found in the atmosphere. Carbon dioxide can be captured from these biological, industrial, and atmospheric processes via many known technologies and can be used for feedstock for the invention.

Zero carbon, low carbon, or ultra-low carbon fuels and chemicals require that fossil fuels are not combusted in the process of producing the fuels and chemicals. This means that any heating of the feeds to the integrated process needs to be by indirect means (cross exchangers) or via electric heating where the electricity comes from a zero carbon or renewable source such as wind, solar, geothermal, or nuclear.

Hydrogen stream 1 and carbon dioxide stream 2 are mixed to form stream 3 in FIG. 1. The ratio of $H_2/CO_2$ is between 2.0 mol/mol to 4.0 mol/mol, more preferably between 3.0 to 4.0 mol/mol. The mixed Reverse Water Gas Shift (RWGS) feedstock can be heated by indirect heat exchange to a temperature of greater than 900° F. It is important that this initial temperature rise is done without the use of direct combustion of a carbon containing gas to provide the heat as that would mean that carbon dioxide was being produced and could possibly negate the impact of converting carbon dioxide to useful fuels and chemicals.

The RWGS feed gas, comprising a mixture of hydrogen and carbon dioxide, is heated to an inlet temperature greater than 1500° F., or preferably greater than 1600° F., at least partially in a preheater outside the main reactor vessel to produce a heated feed gas. FIG. 1 shows that a preheater is labeled as step 4. The preheater step 4 is electrically heated and raises the temperature of the feed gas through indirect heat exchange to greater than 1500° F., and preferably greater than 1600° F. There are numerous ways that the electrical heating of the feed gas can be done. One way is through electrical heating in an electrically heated radiant furnace. In this embodiment, at least a portion of the feed gas passes through a heating coil in a furnace. In the furnace, the heating coil is surrounded by radiant electric heating elements or the gas is passed directly over the heating elements whereby the gas is heated by some convective heat transfer. The electric heating elements can be made from numerous materials. The heating elements may be nickel chromium alloys. These elements may be in rolled strips or wires or cast as zig zag patterns. The elements are typically backed by an insulated steel shell, and ceramic fiber is generally used for insulation. The radiant elements may be divided into zones to give a controlled pattern of heating. Multiple coils and multiple zones may be needed to provide the heat to the feed gas and produce a heated feed gas. Radiant furnaces require proper design of the heating elements and fluid coils to ensure good view factors and good heat transfer. The electricity usage by the radiant furnace should be as low as possible. The electricity usage by the radiant furnace is less than 0.5 MWh (megawatt-hour) electricity/ metric ton (MT) of $CO_2$ in the feed gas; more preferably less than 0.40 MWh/MT $CO_2$; and even more preferably less than 0.20 MWh/MT $CO_2$.

The heated RWGS feed gas stream 5 then is fed into the main RWGS reactor vessel step 6. There are two possible embodiments of the main RWGS reactor vessel. In the first embodiment, the main RWGS reactor vessel is adiabatic or nearly adiabatic and is designed to minimize heat loss, but no added heat is added to the main reactor vessel and the temperature in the main reactor vessel will decline from the inlet to the outlet of the reactor. In the second embodiment, the main RWGS reactor vessel is similarly designed but additional heat is added to the vessel to maintain an isothermal or nearly isothermal temperature profile in the vessel. The main RWGS reactor vessel is a reactor with a length longer than diameter. The entrance to the main reactor vessel is smaller than the overall diameter of the vessel. The main reactor vessel is a steel vessel. The steel vessel is insulated internally to limit heat loss. Various insulations including poured or castable refractory lining or insulating bricks may be used to limit the heat losses to the environment.

A bed of catalyst is inside the main RWGS reactor vessel. The catalyst can be in the form of granules, pellets, spheres, trilobes, quadra-lobes, monoliths, or any other engineered shape to minimize pressure drop across the reactor. Ideally the shape and particle size of the catalyst particles is managed such that pressure drop across the reactor is less than 100 pounds per square inch (psi) [345 kPa] and more preferably less than 20 psi (139 kPa). The size of the catalyst form can have a characteristic dimension of between 1 mm and 10 mm. The catalyst particle is a structured material that is porous material with an internal surface area greater than 40 $m^2/g$, more preferably greater than 80 $m^2/g$ with a preferred surface area of 100 $m^2/g$. Several catalyst materials are possible that can catalyze the RWGS reaction. The primary catalyst studied for RWGS previously were Cu or Pt or Rh dispersed on metal oxide supports. (Daza & Kuhn, *RSC Adv.* 2016, 6, 49675-49691). It has been found that the preferred catalyst is a solid solution catalyst with a transition metal on a metal-alumina spinel.

The RWGS catalyst used in the process is a high-performance solid solution catalyst that is highly versatile, and which efficiently performs the RWGS reaction. The robust, solid solution transition metal catalyst has high thermal stability up to 1,100° C., does not form carbon (coking), and has good resistance to contaminants that may be present in captured $CO_2$ streams. This catalyst exhibits high activity at low transition metal concentrations (5-20 wt. %), compared to other catalysts that require at least 30 wt. % transition metals. Furthermore, the use of expensive precious metals to enhance catalyst performance is not necessary. The manufacturing process for the RWGS catalyst is important as well in that it produces a catalyst that forms a unique solid solution phase, bi-metallic crystalline phase that leads to no segregation of the metal phases. This unique chemical structure leads to enhanced resistance to coking, when compared to conventional metal supported catalysts. This also leads to enhanced resistance to poisons such as sulfur and ammonia. In addition, this catalyst has enhanced catalytic activity at lower surface area compared to monometallic segregated catalyst phase for example Ni on alumina. This catalyst requires no alkali promotion needed to curb the carbon deposition.

Wherein the pressure of the RWGS step and the pressure of the hydrocarbon synthesis or Liquid Fuel Production (LFP) step are within 200 psi of each other, more preferably within 100 psi of each other, or even more preferably 50 psi of each other. Operating the two processes at pressures close to each other limit the required compression of the syngas stream.

The per pass conversion of carbon dioxide to carbon monoxide in the main RWGS reactor vessel is generally between 60 and 90 mole % and more preferably between 70 and 85 mole %. If the embodiment of an adiabatic reactor is used, the temperature in the main RWGS reactor vessel will decline from the inlet to the outlet. The main RWGS reactor vessel outlet temperature is 100° F. to 200° F. less than the main reactor vessel inlet temperature and more preferably between 105 and 160° F. lower than the main reactor inlet temperature. The RWGS Weight Hourly Space Velocity (WHSV) which is the mass flow rate of RWGS reactants ($H_2+CO_2$) per hour divided by the mass of the catalyst in the main RWGS reactor bed is between 1,000 and 50,000 $hr^{-1}$ and preferably between 5,000 and 30,000 $hr^{-1}$.

The gas leaving the main RWGS reactor vessel is the RWGS product gas stream 7. The RWGS product gas comprises carbon monoxide (CO), hydrogen ($H_2$), unreacted carbon dioxide ($CO_2$), and water ($H_2O$). Additionally, the RWGS product gas may also comprise a small quantity of methane ($CH_4$) that was produced in the main reactor vessel by a side reaction.

The RWGS product gas can be used in a variety of ways at this point in the process. The product gas can be cooled and compressed and used in downstream process to produce fuels and chemicals as shown on FIG. 2. The RWGS product gas can also be cooled, compressed step 8, and sent back to the preheater step 4 and fed back to the main reactor vessel step 5. The RWGS product gas can also be reheated in second electric preheater step 9 and sent to a second reactor vessel step 10 where additional conversion of $CO_2$ to CO can occur.

Figure 2:
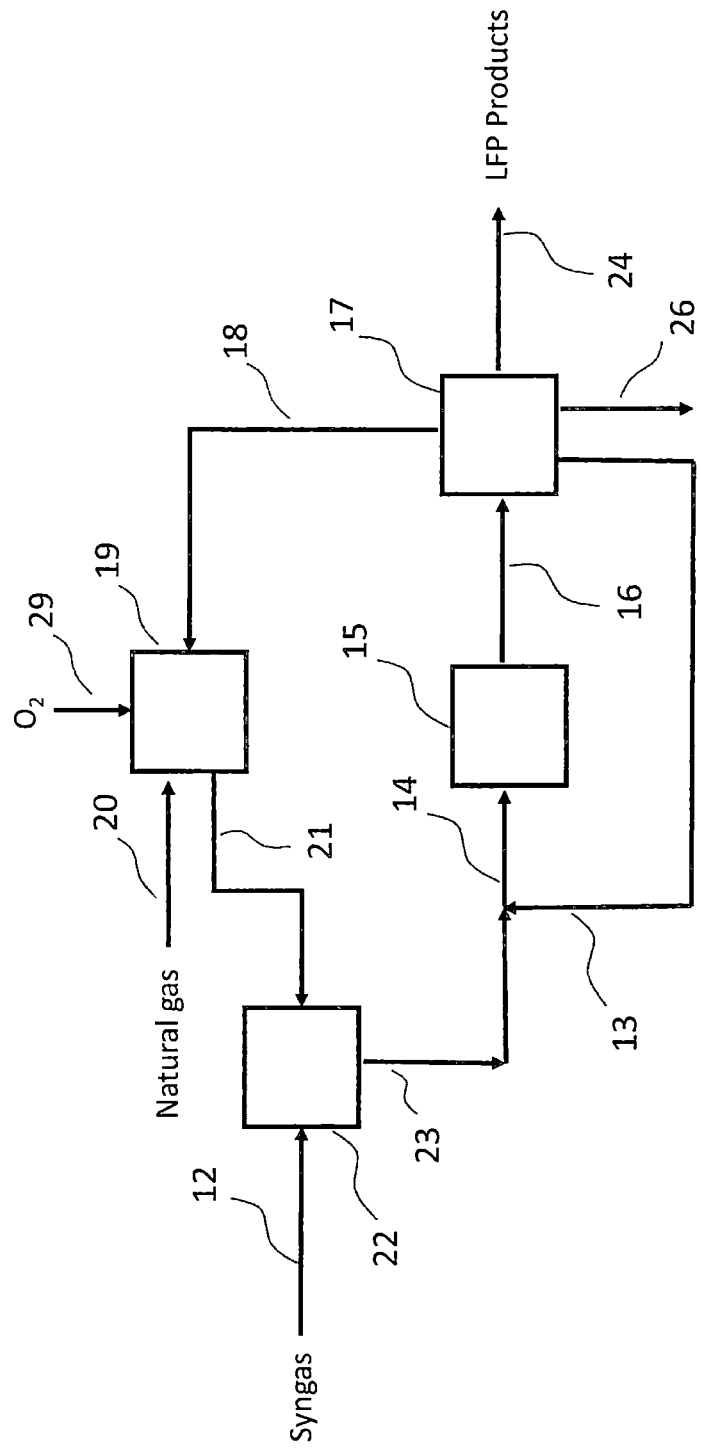

FIG. 2 shows the hydrocarbon synthesis step. This is also known as the Liquid Fuel Production (LFP) step. The LFP reactor converts CO and $H_2$ into long chain hydrocarbons that can be used as liquid fuels and chemicals. This reactor uses a unique catalyst for production of liquid fuel range hydrocarbons from syngas. Syngas stream 12 from syngas cooling and condensing step 22 in FIG. 2 (and optional compression step 11 in FIG. 1) is blended with tailgas stream 13 to produce an LFP reactor feed stream 14. The LFP reactor feed comprises hydrogen and carbon monoxide. Ideally the hydrogen to carbon monoxide ratio in the stream is between 1.9 and 2.2 mol/mol. The LFP reactor step 15 is a multi-tubular fixed bed reactor system. Each LFP reactor tube can be between 13 mm and 26 mm in diameter. The length of the reactor tube is generally greater than 6 meters in length and more preferably greater than 10 meters in length. The LFP reactors are generally vertically oriented with LFP reactor feed entering at the top of the LFP reactor. However, horizontal reactor orientation is possible in some circumstances and setting the reactor at an angle may also be advantageous in some circumstances where there are height limitations. Most of the length of the LFP reactor tube is filled with LFP catalyst. The LFP catalyst may also be blended with diluent such as silica or alumina to aid in the distribution of the LFP reactor feed into and through the LFP reactor tube. The chemical reaction that takes place in the LFP reactor produces an LFP product gas that comprises most hydrocarbon products from five to twenty-four carbons in length ($C_5$-$C_{24}$ hydrocarbons) as well as water, although some hydrocarbons are outside this range. It is important that the LFP reactor not produce any significant amount of carbon dioxide. Less than 2% of the carbon monoxide in the LFP reactor feed should be converted to carbon dioxide in the LFP reactor. It is also important that only a limited amount of the carbon monoxide in the LFP reactor feed be converted to hydrocarbons with a carbon number greater than 24. Less than 25% of the hydrocarbon fraction of the LFP product should have a carbon number greater than 24. More preferably less than 10 wgt % of the hydrocarbon fraction of the LFP product should have a carbon number greater than 24. Even more preferably, less than 4 wgt % of the hydrocarbon fraction of the LFP product should have a carbon number greater than 24. Even more preferably, less than 1 wgt % of the hydrocarbon fraction of the LFP product should have a carbon number greater than 24. As discussed above, Fischer-Tropsch (F-T) processes generally make hydrocarbon products that are from 1 to 125 carbon atoms in length. The LFP catalyst used does not produce heavy hydrocarbons with the same yield as other catalysts used in the F-T process. In some embodiments of the invention, the LFP catalyst has insignificant activity for the conversion of conversion of carbon monoxide to carbon dioxide via the water-gas-shift reaction. In some embodiments of the invention, the water gas shift conversion of carbon monoxide to carbon dioxide is less than 5% of the carbon monoxide in the feed. In some embodiments, the LFP catalyst comprises cobalt as the active metal. In some embodiments, the LFP catalyst comprises iron as the active metal. In some embodiments, the LFP catalyst comprises combinations of iron and cobalt as the active metal. The LFP catalyst is supported on a metal oxide support that chosen from a group of alumina, silica, titania, activated carbon, carbon nanotubes, zeolites or other support materials with sufficient size, shape, pore diameter, surface area, crush strength, effective pellet radius, or mixtures thereof. The catalyst can have various shapes of various lobed supports with either three, four, or five lobes with two or more of the lobes being longer than the other two shorter lobes, with both the longer lobes being symmetric. The distance from the mid-point of the support or the mid-point of each lobe is called the effective pellet radius which is an important parameter to achieve the desired selectivity to the $C_5$ to $C_{24}$ hydrocarbons. The LFP catalyst promoters may include one of the following: nickel, cerium, lanthanum, platinum, ruthenium, rhenium, gold, or rhodium. The LFP catalyst promoters are less than 1 wt. % of the total catalyst and preferably less than 0.5 wt. % and even more preferably less than 0.1 wt. %.

The LFP catalyst support has a pore diameter greater than 8 nanometers (nm), a mean effective pellet radius of less than 600 microns, a crush strength greater than 3 lbs/mm and a BET surface area of greater than 100 $m^2/g$. The catalyst after metal impregnation has a metal dispersion of about 4%. Several types of supports have been found to maximize the $C_5$-$C_{24}$ hydrocarbon yield. These include alumina/silica combinations, activated carbon, alumina, carbon nanotubes, and/or zeolite-based supports.

The LFP fixed bed reactor is operated in a manner to maximize the $C_5$-$C_{24}$ hydrocarbon yield. The LFP reactor in one embodiment is operated at pressures between 150 to 450 psi. The reactor is operated over a temperature range from 350 to 460° F. and more typically at around 410° F. The reaction is exothermic. The temperature of the reactor is maintained inside the LFP reactor tubes by the reactor tube bundle being placed into a heat exchanger where boiling steam is present on the outside of the LFP reactor tubes. The steam temperature is at a lower temperature than the LFP reaction temperature so that heat flows from the LFP reactor tube to the lower temperature steam. The steam temperature is maintained by maintaining the pressure of the steam. The steam is generally saturated steam. In an alternate embodiment, the catalytic reactor can be a slurry reactor, microchannel reactor, fluidized bed reactor, or other reactor types known in the art.

The CO conversion in the LFP reactor is maintained at between 30 to 80 mole % CO conversion per pass. CO can be recycled for extra conversion or sent to a downstream additional LFP reactor. The carbon selectivity to $CO_2$ is minimized to less than 4% of the converted CO and more preferably less than 1%. The carbon selectivity for C5-C24 hydrocarbons is between 60 and 90%. The LFP reactor product gas stream 16 contains the desired C5-C24 hydrocarbons, which are condensed as liquid fuels and water, as well as unreacted carbon monoxide, hydrogen, a small amount of C1-C4 hydrocarbons, and a small amount of C24+ hydrocarbons stream 24. The desired product is separated from the stream by cooling, condensing the product and/or distillation or any other acceptable means step 17. The unreacted carbon monoxide, hydrogen, and C1-C4 hydrocarbons stream 18 are part of the feed to the Auto-thermal Reformer step 19.

FIG. 2 also shows the auto-thermal reformer (ATR) step 20 section of the process. In the Auto-thermal Reformer (ATR), the ATR hydrocarbon feed comprises carbon monoxide, hydrogen, and C1-C4 hydrocarbons. The Auto-thermal reforming of natural gas that is predominately methane (C1) to carbon monoxide and hydrogen has been commercially practiced for many years. See K. Aasberg-Petersen et al., Journal of Natural Gas Science and Engineering 3 (2011) 423-459.

In one embodiment of the invention, the ATR hydrocarbon feed comprises natural gas steam 20 and the unreacted carbon monoxide, hydrogen, and C1-C4 hydrocarbons stream 18. The natural gas comprises methane and may contain light hydrocarbons as well as carbon dioxide. In this embodiment, the fuel and chemicals produced may not zero carbon fuels but will still have an improved carbon intensity over traditional fuels and chemicals. The natural gas in the ATR feed is converted to syngas (including a large percentage of hydrogen). This reduces the amount of water that needs to be electrolyzed to produce hydrogen and reduces the size of the electrolyzer. This embodiment may be more economically feasible to produce low carbon fuels and chemicals. In the ATR hydrocarbon feed the ratio of natural gas to LFP unreacted carbon monoxide, hydrogen, and C1-C4 hydrocarbons should be less than 2.0 kg/kg. More preferably, ratios should be less than 1.25 kg/kg.

The ATR used in this invention is to produce a product that is high in carbon monoxide and the carbon dioxide in the product gas is less than 10 mol %. The ATR oxidant feed comprises steam and oxygen where the oxygen is produced by the electrolysis of water. The ATR oxidant feed and the ATR hydrocarbon feed are preheated and then reacted in an ATR burner where the oxidant and the hydrocarbon are partially oxidized at temperatures in the burner of greater than 2000° C. The ATR reactor can be divided into three zones; the Combustion zone (or burner) where at least portion of the ATR hydrocarbon feedstock is fully combusted to water and carbon dioxide; the thermal zone where thermal reactions occur. In the thermal zone further conversion occurs by homogeneous gas-phase-reactions. These reactions are slower reactions than the combustion reactions like CO oxidation and pyrolysis reactions involving higher hydrocarbons.

The main overall reactions in the thermal zone are the homogeneous gas-phase steam hydrocarbon reforming and the shift reaction. In the catalytic zone, the final conversion of hydrocarbons takes place through heterogeneous catalytic reactions including steam methane reforming and water gas shift reaction. The resulting ATR product gas has a composition that is close to the predicted thermodynamic equilibrium composition. The actual ATR product gas composition is the same as the thermodynamic equilibrium composition within a difference of less than 70 C. This is the so-called equilibrium approach temperature. To keep the amount of $CO_2$ produced in the ATR to a minimum, the amount of steam in the ATR oxidant feed needs to be kept as low as possible that still results in a low soot ATR product gas that is close to the equilibrium predicted composition. Typically, the total steam to carbon ratio (mol/mol) in the combined ATR feed (oxidant+hydrocarbon) should be between 0.4 to 1.0, with the optimum being around 0.6.

The ATR product leaves the ATR catalytic zone at temperatures more than 800° C. The ATR product step 21 is cooled to lower temperatures through a waste heat boiler step 22 where the heat is transferred to generate steam. This steam, as well as the lower pressure steam produced by the LFP reactor, can be used to generate electricity.

Suitable ATR catalysts for the catalytic zone reactions are typically nickel based. The novel solid solution catalyst described previously can be used as an ATR catalyst. Other suitable ATR catalysts are nickel on alpha phase alumina or magnesium alumina spinel ($MgAl_2O_4$) are used with or without precious metal promoters where the precious metal promoter comprises gold, platinum, rhenium, or ruthenium. Spinels have a higher melting point and a higher thermal strength and stability than the alumina-based catalysts.

The ATR product stream 23 can be blended with the RWGS product and be used as LFP reactor feed. This results in a high utilization of the original carbon dioxide to C5 to C24 hydrocarbon products.

In some embodiments, the LFP product gas is not suitable as a direct feed to the ATR and must be pre-reformed. In those cases, the LFP product gas comprising the unreacted carbon monoxide, hydrogen, C1-C4 hydrocarbons and $CO_2$ comprise the pre-reformer hydrocarbon feed gas. The higher the higher hydrocarbons and carbon oxides in the stream may require the use of a pre-reformer instead of directly being used in as ATR hydrocarbon feed. The pre-reformer is generally an adiabatic reactor. The adiabatic pre-reformer converts higher hydrocarbons in the pre-reformer feed into a mixture of methane, steam, carbon oxides and hydrogen that are then suitable as ATR hydrocarbon feed. One benefit of using a pre-reformer is that it enables higher ATR hydrocarbon feed pre-heating that can reduce the oxygen used in the ATR. The resulting integrated process as described above results in high conversion of carbon dioxide to C5-C24 hydrocarbon products that are suitable as fuels or chemicals.

Certain Method Embodiments

The following are certain embodiments of processes for the conversion of carbon dioxide, water, and electricity into low or zero carbon high quality fuels and chemicals: 1. Water is fed into an electrolysis system powered using renewable electricity.

Carbon dioxide is captured from a source. Hydrogen and carbon dioxide are mixed to form a stream (Reverse Water Gas Shift feedstock or "RWGS" feedstock) that is typically heated and then fed into a RWGS reactor vessel that includes the solid solution catalyst. The RWGS reactor converts the feedstock to an RWGS product gas comprising carbon monoxide, hydrogen, unreacted carbon dioxide and water. The RWGS product gas is cooled, compressed, and fed into a Liquid Fuels Production ("LFP") system or otherwise called the hydrocarbon synthesis step. The LFP system converts RWGS product gas (either purified or not) into hydrocarbon products, where more than 50 percent of the products are C5 to C24 hydrocarbons. Wherein the pressure of the RWGS step and the pressure of the hydrocarbon synthesis step are within 200 psi of each other, more preferably within 100 psi of each other, or even more preferably within 50 psi of each other.

2. Water is fed into an electrolysis system powered using renewable electricity. Carbon dioxide is captured from a source. Hydrogen and carbon dioxide are mixed to form a stream (Reverse Water Gas Shift feedstock or "RWGS" feedstock) that is typically heated and then fed into a RWGS reactor vessel that includes a nickel-based solid solution catalyst. The RWGS reactor converts the feedstock to an RWGS product gas comprising carbon monoxide, hydrogen, unreacted carbon dioxide and water. One or more C1-C4 hydrocarbons, carbon monoxide and hydrogen are fed into an auto-thermal reformer ("ATR") to provide an ATR product stream. The RWGS product gas (either purified or not) is blended with the ATR product stream (either purified or not) and fed into the Liquid Fuels Production ("LFP") system. The LFP system converts the blended RWGS and ATR products into hydrocarbon products, where more than 50 percent of the products are C4 to C24 hydrocarbons.

3. Water is fed into an electrolysis system powered using renewable electricity. Carbon dioxide is captured from a source. Hydrogen and carbon dioxide are mixed to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4 hydrocarbons, carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system that includes a Fischer-Tropsch catalyst or other catalyst or catalysts that produces hydrocarbons from syngas. The LFP system converts the blended RWGS and ATR products into hydrocarbon products, where more than 50 percent of the products are C5 to C24 hydrocarbons.

4. Water is fed into an electrolysis system powered using renewable electricity. Carbon dioxide is captured from a source, where the source is an industrial manufacturing plant that produces ammonia for fertilizer, a cement plant, an ethanol plant that converts corn, rice or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. The RWGS product gas is cooled, compressed and fed into a Liquid Fuels Production ("LFP") system that includes a catalyst or other catalyst that produces hydrocarbons from syngas. The LFP system converts RWGS product gas (either purified or not) into hydrocarbon products, where more than 50 percent of the products are C5 to C24 hydrocarbons.

5. Water is fed into an electrolysis system powered using renewable electricity. Carbon dioxide is captured from a source, where the source is an industrial manufacturing plant that produces ammonia for fertilizer, a cement plant, an ethanol plant that converts corn. rice or wheat into ethanol, a petroleum refining plant, a chemical plant, a power plant that generates electricity, anaerobic digestion, or the atmosphere. Hydrogen and carbon dioxide are mixed to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4+ hydrocarbons (e.g., methane), carbon monoxide and hydrogen are fed into an auto-thermal reformer ("ATR") to provide an ATR product stream. The RWGS product gas (either purified or not) is blended with the ATR product stream (either purified or not) and fed into a catalytic system that produces methanol.

6. Water is fed into an electrolysis system powered using renewable electricity. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4+ hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a process that produces ammonia from syngas.

7. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. The RWGS product gas is cooled, compressed, and fed into a Liquid Fuels Production ("LFP") system that may include a Fischer-Tropsch catalyst that produces primarily wax with hydrocarbons ranging from C5-C100+.

8. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed to form a stream (Reverse Water Gas Shift feedstock or "RWGS" feedstock) that is typically heated and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4 hydrocarbons (e.g., methane), carbon monoxide and hydrogen are fed into an auto-thermal reformer ("ATR") to provide an ATR product stream. The RWGS product gas (either purified or not) is blended with the ATR product stream (either purified or not) and fed into process that produces ammonia.

9. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed to form a stream (Reverse Water Gas Shift feedstock or "RWGS" feedstock) that is typically heated and then fed into a RWGS reactor vessel that includes a solid solution catalyst that includes a transition metal. The RWGS reactor converts the feedstock to an RWGS product gas comprising carbon monoxide, hydrogen, unreacted carbon dioxide and water. One or more C1-C4 hydrocarbons (e.g., methane), carbon monoxide and hydrogen are fed into an auto-thermal reformer ("ATR") that includes a solid solution catalyst to provide an ATR product stream. The RWGS product gas (either purified or not) is blended with the ATR product stream (either purified or not) and fed into a Liquid Fuels Production ("LFP") system that includes a catalyst that produces hydrocarbons from syngas. The LFP system converts the blended RWGS and ATR products into hydrocarbon products, where more than 70 percent of the products are C5 to C24 hydrocarbons.

10. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, natural gas processing plant, a power plant that generates electricity, anaerobic digestion, or the atmosphere. Hydrogen and carbon dioxide are mixed to form a stream (Reverse Water Gas Shift feedstock or "RWGS" feedstock) that is heated to an inlet temperature greater than 1400° F., where the heat is not provided by direct combustion of a carbon containing gas, and then fed into a RWGS reactor vessel that includes a nickel solid solution catalyst. The RWGS reactor converts the feedstock to an RWGS product gas comprising carbon monoxide, hydrogen, unreacted carbon dioxide and water. The RWGS product gas is cooled, compressed and system that produces ammonia, methanol, or liquid hydrocarbons.

11. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed to form a stream (Reverse Water Gas Shift feedstock or "RWGS" feedstock) that is heated to an inlet temperature greater than 1000° F., where the heat is not provided by direct combustion of a carbon containing gas, and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system that includes a fuel production catalyst that uses a combination of nickel and cobalt. The LFP system converts the blended RWGS and ATR products into hydrocarbon products, where more than 50 percent of the products are C5 to C24 hydrocarbons.

12. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into a RWGS reactor vessel that includes a transition metal based solid solution catalyst. The RWGS reactor converts the feedstock to an RWGS product gas comprising carbon monoxide, hydrogen, unreacted carbon dioxide and water. The RWGS product gas is cooled, compressed, and fed into a chemical production facility.

13. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into a RWGS reactor vessel that includes a nickel solid solution catalyst. The RWGS reactor converts the feedstock to an RWGS product gas comprising carbon monoxide, hydrogen, unreacted carbon dioxide and water. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a system that uses a Fischer-Tropsch catalyst that produces a high hydrocarbon wax as a primary product.

14. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1200° F. using any type of electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The RWGS reactor converts the feedstock to an RWGS product gas comprising carbon monoxide, hydrogen, unreacted carbon dioxide and water. The RWGS product gas is cooled, compressed, and fed into a Liquid Fuels Production ("LFP") system that includes a Fischer-Tropsch catalyst or other catalyst that produces hydrocarbons from syngas. The LFP system converts RWGS product gas (either purified or not) into hydrocarbon products, where more than 50 percent of the products are C4 to C24 hydrocarbons.

15. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, natural gas processing plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a solid solution catalyst. The RWGS reactor converts the feedstock to an RWGS product gas comprising carbon monoxide, hydrogen, unreacted carbon dioxide and water. One or more C1-C3 hydrocarbons (e.g., methane), carbon monoxide and hydrogen are fed into an auto-thermal reformer ("ATR"). The RWGS product gas (either purified or not) is blended with the ATR product stream (either purified or not) and fed into a methanol production system.

16. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The RWGS product gas is cooled, compressed, and fed into a Liquid Fuels Production ("LFP") system that includes a catalyst that produces hydrocarbons from syngas. The LFP system converts RWGS product gas (either purified or not) into hydrocarbon products, where more than 50 percent of the products are C5 to C24 hydrocarbons.

17. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, natural gas processing plant, a power plant that generates electricity, anaerobic digestion, or the atmosphere. Hydrogen and carbon dioxide are mixed together to form a stream (Reverse Water Gas Shift feedstock or "RWGS"

feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. One or more C1-C3 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into syngas conversion system consisting of either a methanol synthesis process, ammonia production process, Fischer-Tropsch process for the production of wax and other hydrocarbons, or other chemical or fuel production.

18. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 100 pounds per square inch or less than 50 pounds per-square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 30 and 90 mole % or between 50 and 70 mole %, and the RWGS Weight Hourly Space Velocity is between 1,000 and 50,000 $hr^{-1}$ or between 5,000 and 30,000 $hr^{-1}$. The RWGS product gas is cooled, compressed, and fed into a Liquid Fuels Production ("LFP") system that includes a catalyst that produces hydrocarbons from syngas. The LFP system converts RWGS product gas (either purified or not) into hydrocarbon products, where more than 50 percent of the products are C5 to C24 hydrocarbons.

19. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or a low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, natural gas processing plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1000° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a transition metal based solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity is between 1,000 and 50,000 $hr^{-1}$ and more preferably 5,000 to 30,000 $hr^{-1}$. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either, purified or not) is blended with the ATR product stream (either purified or not) and fed into a Liquid Fuels Production ("LFP") system that includes a Fischer-Tropsch catalyst or other catalyst that produces hydrocarbons from syngas. The LFP system converts the blended RWGS and ATR products into hydrocarbon products, where more than 50 percent of the products are C4 to C24 hydrocarbons.

20. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable or low carbon energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity is between 1,000 and 50,000 hr$^{-1}$ and more preferably 5,000 to 30,000 hr$^{-1}$. The RWGS product gas is cooled, compressed, and fed into a Liquid Fuels Production ("LFP") system, along with recycled syngas, that includes a catalyst that produces hydrocarbons from syngas. The reactor is a multi-tubular fixed bed reactor system where each reactor tube is between 13 mm and 26 mm I diameter and has a length greater than 6 meters or greater than 10 meters in length.

21. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a transition metal based solid solution catalyst. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 90 mole % or between 30 and 70 mole %, and the RWGS Weight Hourly Space Velocity is between 1,000 and 50,0000 hr$^{-1}$ and more preferably between 5,000 to 30,000 hr$^{-1}$. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system, along with recycled syngas, that includes a Fischer-Tropsch catalyst or other catalyst that produces hydrocarbons from syngas. The reactor is a multi-tubular fixed bed reactor system where each reactor tube is between 13 mm and 26 mm I diameter and has a length greater than 6 meters or greater than 10 meters in length. The LFP system converts the blended RWGS and ATR products into hydrocarbon products, where more than 50 percent of the products are C5 to C24 hydrocarbons.

23. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 90 mole % or between 40 and 80 mole %, and the RWGS Weight Hourly Space Velocity between 1,000 and 50,000 hr$^{-1}$ and more preferably 5,000 to 30,000 hr$^{-1}$. The RWGS product gas is cooled, compressed, and fed into a Liquid Fuels Production ("LFP") system, along with recycled syngas, that includes a catalyst that produces hydrocarbons from syngas. The reactor is a multi-tubular fixed bed reactor system where each reactor tube is between 13 mm and 26 mm I diameter and has a length greater than 6 meters or greater than 10 meters in length. The LFP system converts RWGS product gas (either purified or not) into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24.

24. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity between 1,000 and 50,000 hr$^{-1}$ and more preferably between 5,000 to 30,000 hr$^{-1}$. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system, along with recycled syngas, that includes a catalyst that produces hydrocarbons from syngas. The reactor is a multi-tubular fixed bed reactor system where each reactor tube is between 13 mm and 26 mm I diameter and has a length greater than 6 meters or greater than 10 meters in length. The LFP system converts the blended RWGS and ATR products into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24.

25. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 100 pounds per square inch or less. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity between 1,000 and 50,000 $hr^{-1}$ and more preferably 5,000 to 30,000 $hr^{-1}$. The RWGS product gas is cooled, compressed, and fed into a Liquid Fuels Production ("LFP") system, along with recycled syngas, that includes a catalyst that produces hydrocarbons from syngas. The LFP catalyst support has a pore diameter greater than 8 nanometers, a mean effective pellet radius of less than 60 micrometers, a crush strength greater than 3 lbs/mm and a BET surface area greater than 80 $m^2/g$, greater than 90 $m^2/g$, greater than 100 $m^2/g$, greater than 125 $m^2/g$ or greater than 150 $m^2/g$; and the metal dispersion of the catalyst on the support is between 2% and 4% or about 3%. The reactor is a multi-tubular fixed bed reactor system where each reactor tube is between 13 mm and 26 mm I diameter and has a length greater than 6 meters or greater than 10 meters in length. The LFP system converts RWGS product gas (either purified or not) into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24.

26. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a natural gas processing plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 90 mole % or between 50 and 85 mole %, and the RWGS Weight Hourly Space Velocity between 1,000 and 50,000 $hr^{-1}$ and more preferably between 5,000 to 30,000 $hr^{-1}$. One or more C1-C4 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system, along with a catalyst that produces hydrocarbons from syngas. The LFP catalyst support has a pore diameter greater than 8 nanometers, a mean effective pellet radius of less than 60 micrometers, a crush strength greater than 3 lbs/mm and a BET surface area greater than 80 $m^2/g$, greater than 90 $m^2/g$, greater than 100 $m^2/g$, greater than 125 $m^2/g$ or greater than 150 $m^2/g$; and the metal dispersion of the catalyst on the support is between 2% and 4% or about 3%. The reactor is a multi-tubular fixed bed reactor system where each reactor tube is between 13 mm and 26 mm I diameter and has a length greater than 6 meters or greater than 10 meters in length. The LFP system converts the blended RWGS and ATR products into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24.

27. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity between 1,000 and 50,000 $hr^{-1}$ and more preferably 5,000 to 30,000 $hr^{-1}$. The RWGS product gas is cooled, compressed and fed into a Liquid Fuels Production ("LFP") system, along with recycled syngas, that includes a catalyst that produces hydrocarbons from syngas. The LFP catalyst support has a pore diameter greater than 8 nanometers, a mean effective pellet radius of less than 60 micrometers, a crush strength greater than 3 lbs/mm and a BET surface area greater than 80 $m^2/g$, greater than 90 $m^2/g$, greater than 100 $m^2/g$, greater than 125 $m^2/g$ or greater than 150 $m^2/g$; and the metal dispersion of the catalyst on the support is between 2% and 4% or about 3%. The reactor is a multi-tubular fixed bed reactor system where each reactor tube is between 13 mm and 26 mm I diameter and has a length greater than 6 meters or greater than 10 meters in length. The LFP system converts RWGS product gas (either purified or not) into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24. The CO conversion in the LFP reactor is maintained between 30 to 80 mole % CO conversion per pass, and the carbon selectivity to $CO_2$ is minimized to less than 4% or less than 1% of the converted CO.

28. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 90 mole % or between 60 and 90 mole %, and the RWGS Weight Hourly Space Velocity is between 1,000 and 50,000 $hr^{-1}$ and more preferably 5,000 to 30,000 $hr^{-1}$. One or more C1-C3 hydrocarbons (e.g., methane), carbon monoxide and hydrogen are fed into an auto-thermal reformer ("ATR") that includes a nickel solid solution catalyst to provide an ATR product stream. The RWGS product gas (either purified or not) is blended with the ATR product stream (either purified or not) and fed into a Liquid Fuels Production ("LFP") system, along with recycled syngas, that includes a catalyst that produces hydrocarbons from syngas. The LFP catalyst support has a pore diameter greater than 8 nanometers, a mean effective pellet radius of less than 60 micrometers, a crush strength greater than 3 lbs/mm and a BET surface area greater than 80 $m^2/g$, greater than 90 $m^2/g$, greater than 100 $m^2/g$, greater than 125 $m^2/g$ or greater than 150 $m^2/g$; and the metal dispersion of the catalyst on the support is between 2% and 4% or about 3%. The reactor is a multi-tubular fixed bed reactor system where each reactor tube is between 13 mm and 26 mm I diameter and has a length greater than 6 meters or greater than 10 meters in length. The LFP system converts the blended RWGS and ATR products into hydrocarbon products, where more than 50 percent of the products are C4 to C24 hydrocarbons. Less than 2% of the carbon monoxide in the LFP reactor feed is converted to carbon dioxide in the LFP reactor, and less than 10 wgt % or less than 4 wgt % of the hydrocarbon fraction of the LFP product has a carbon number greater than 24. The CO conversion in the LFP reactor is maintained between 30 to 80 mole % CO conversion per pass, and the carbon selectivity to $CO_2$ is minimized to less than 4% or less than 1% of the converted CO.

29. Water is fed into an electrolysis system powered using renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The shape and particle size of the catalyst particles is managed such that the pressure drop across the reactor is less than 50 pounds per square inch or less than 20 pounds per square inch. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 90 mole % or between 30 and 70 mole %, and the RWGS Weight Hourly Space Velocity is between 1 and 1,000-50,000 hr$^{-1}$ and more preferably 5,000 to 30,000 hr$^{-1}$. The RWGS product gas is cooled, compressed and fed into a Liquid Fuels Production ("LFP") system, along with recycled syngas, that includes another catalyst that produces hydrocarbons from syngas. The hydrocarbons produced in this process, or a portion thereof, are used as fuels; the fuels have a percent reduction in lifecycle Greenhouse Gas Emissions compared to the average lifecycle Greenhouse Gas Emissions for petrodiesel (produced from the fractional distillation of crude oil between 200° C. and 350° C. at atmospheric pressure, resulting in a mixture of carbon chains that typically contain between 9 and 25 carbon atoms per molecule) of at least 10 percent, at least 20 percent, at least 30 percent, at least 40 percent, at least 50 percent, at least 60 percent, at least 70 percent, at least 80 percent or at least 90 percent.

30. Water is fed into an electrolysis system powered by renewable electricity, where the electrolyzer of the electrolysis system operates using alkaline electrolysis, membrane electrolysis or high temperature electrolysis and the renewable electricity is derived from wind, solar, geothermal, or nuclear as a renewable energy source. Carbon dioxide is captured from a source, where the source is an industrial manufacturing plant that produces ammonia for fertilizer, a cement plant, an ethanol plant that converts corn or wheat into ethanol, a petroleum refining plant, a chemical plant, a power plant that generates electricity, anaerobic digestion, or the atmosphere. Hydrogen and carbon dioxide are mixed together to form a stream (Reverse Water Gas Shift feedstock or "RWGS" feedstock) that is heated to an inlet temperature greater than 1400° F. using radiant electric heating elements that have electricity usage less than 0.5 MWh electricity/metric ton, 0.40 MWh electricity/metric ton or 0.20 MWh electricity/metric ton of $CO_2$ in the feed gas, where the heat is not provided by direct combustion of a carbon containing gas, and then fed into an adiabatic or isothermal RWGS reactor vessel that includes a nickel solid solution catalyst. The RWGS reactor converts the feedstock to an RWGS product gas comprising carbon monoxide, hydrogen, unreacted carbon dioxide and water. The per pass conversion of carbon dioxide to carbon monoxide in the RWGS reactor vessel is between 15 and 75 mole % or between 30 and 70 mole %, and the RWGS Weight Hourly Space Velocity between 1,000 and 50,000 hr$^{-1}$ and more preferably 5,000 to 30,000 hr$^{-1}$. One or more C1-C4 hydrocarbons (e.g., methane), carbon monoxide and hydrogen are fed into an auto-thermal reformer ("ATR") that includes a solid solution catalyst to provide an ATR product stream. The RWGS product gas (either purified or not) is blended with the ATR product stream (either purified or not) and fed into a system that produces fuels or chemicals. The fuels or chemicals produced in this process, or a portion thereof, have a percent reduction in lifecycle Greenhouse Gas Emissions compared to the average lifecycle Greenhouse Gas Emissions for products produced from petroleum of at least 10 percent, at least 20 percent, at least 30 percent, at least 40 percent, at least 50 percent, at least 60 percent, at least 70 percent, at least 80 percent or at least 90 percent.

EXAMPLES

FIGS. 1-2 show the integrated process for the conversion of carbon dioxide, water, and electricity into renewable fuels and chemicals.

The inlets to the process are: 1) 1919 Metric Tons/day (MT/D) of carbon dioxide; 1214 MT/D of fresh water; and 3) 721.5 MW of renewable electricity.

Figure 3:
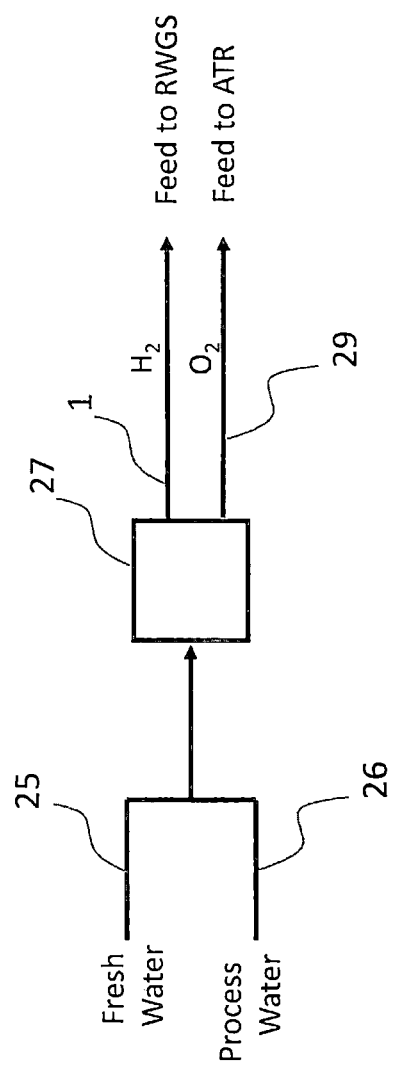

On FIG. 3, the fresh water (stream 25) is blended with 1497 MT/D of process (or recycled) water (stream 26) from the process. The electrolyzer feed of fresh and recycled water is 2711 MT/D of total water. The alkaline electrolyzer step 27 operates at 60 psig and 70° F. The electrolyzer product is 303 MT/D of hydrogen (stream 28) and 2408 MT/D of oxygen (stream 29). The electrolyzer uses 648.1 MW of electricity for an electrolyzer energy usage of 51.3 MWh/MT of hydrogen produced. The hydrogen (FIG. 1 stream 1, 303 MT/D) is mixed with carbon dioxide (stream 2) to become the RWGS feed (stream 3). The carbon dioxide (stream 2) is a mixture of fresh carbon dioxide (stream 2, 1919 MT/D) and recycled carbon dioxide (734 MT/D). The molar ratio of $H_2$ to $CO_2$ in the RWGS feed is 2.5 and within the desired range. The initial RWGS feed (stream 3) is at a pressure of 60 psig and a temperature of 66° F. Stream 3 is heated via indirect heat exchange in two separate heat exchangers step 4 to raise the temperate to 984 F (stream 5). An electric radiant furnace is used to heat the gases to 1600° F. The electric radiant furnace uses 30.7 MW of electricity and has an electricity usage of 0.278 MWh/MT $CO_2$ in the product stream or the final RWGS feed stream (stream 5). The RWGS reactor (step 6) is a refractory lined vessel or a grouping of parallel reactors. The RWGS reactor is filled with catalyst. The RWGS catalyst used in this example is a solid solution catalyst where the only transition metals are used. The RWGS reactor outlet pressure is 10 psi lower than the inlet pressure of 55 psig. The RWGS outlet temperature is 152° F. lower than the 1600° F. inlet temperature. The $CO_2$ conversion is 70 mol %. 92 mol % of the converted $CO_2$ is converted to CO (92% selectivity to CO) while 8% of the converted $CO_2$ is converted to methane via a side reaction.

The RWGS reactor product gas (stream 7) in this example is reheated in back to 1600° F. in an optional $2^{nd}$ heater and RWGS bed (steps 9 and 10 respectively). This heater step 9 is an electrically heated radiant furnace. Step 9 consumes 7.3 MW of electricity for an electricity usage of 0.22 MWh/MT $CO_2$ in the feed. For this example, the re-heated gas is then fed to a second RWGS reactor (step 10). The second RWGS reactor has a 10 psi pressure drop and a temperature decline of 108° F. The $CO_2$ conversion is 7 mol %.

The second RWGS reactor outlet is a syngas mixture with an approximate bulk composition of 49 mol % $H_2$, 20 mol % CO, 1 mol % methane, 8 mol % $CO_2$, 22 mol % water at a temperature of 1492° F. This steam is cooled to 1256° F. via indirect heat exchange (step 11) and is blended with syngas produced by the Auto-thermal reformer (ATR) to become the combined feed to syngas cooling and syngas compression part of the process.

FIG. 2 shows the ATR portion of the process. The ATR has an ATR hydrocarbon feed (stream 18) that comprises the tail gases from the LFP portion of the facility with a flowrate of 855 MT/D and a molar composition of 21% hydrogen, 12% CO, 42% methane, 1% ethane, 2% propane, 1% butanes, 1% pentanes, 1% hexanes, and 18% carbon dioxide. The ATR oxidant feed (stream 29) is 335 MT/D of oxygen that was produced by the electrolyzer. The ATR hydrocarbon feed is blended with 255 MT/D of superheated steam at a temperature of 343 F. Steam while an oxidant is blended with the ATR hydrocarbon feed prior to the ATR burner. This stream is heated via ATR product cross heat exchange and this stream and the oxygen are combusted at the ATR burner and the combustion products pass through the ATR catalyst bed and leave the ATR at or near the equilibrium predicted composition at an exit temperature of 1832 F (stream 21). The ATR operates at a feed steam to carbon ratio of 0.53 where the ratio is moles of steam to moles of carbon from any source in the feed (including $CO_2$ and CO). Soot and carbon formation are minimized by the use a Ni on Mg spinel catalyst with gold promoter and a low operating pressure of 58 psig. The molar composition of the ATR product stream (stream 21) is 46% hydrogen, 27% CO, 7% Carbon Dioxide, and 20% water. The syngas hydrogen to carbon monoxide ratio is 1.7. The ATR product stream is cooled via cross exchange to 1251° F.

The product stream from the ATR is blended syngas from the RWGS reactor system and fed to the Syngas Cooling and Compression section of the plant. The combined syngas is cooled via steam boilers. Some of the steam from the steam system was used to blend in the ATR hydrocarbon feed. The stream is also cooled by air fan coolers. Water is removed from the stream as syngas condensate. Three stage compression is used to raise the pressure of the syngas to 340 psig and a temperature of 338° F. The syngas leaves as Syngas to LFP at a rate of 3093 MT/D with a molar composition of approximately 61% hydrogen, 28% carbon monoxide, 10% carbon dioxide, and 1% water. The syngas compression requires electricity. The electricity usage of the syngas compressors is 34.0 MW.

FIG. 2 shows the LFP portion of the process Feed Syngas stream 23 (3093 MT/D) is blended with an LFP recycle stream (stream 13) of 19,185 MT/D. The molar composition of the recycle gas is about 13% hydrogen, 7% carbon monoxide, 26% methane, 48% carbon dioxide, 1% water, 1% ethane, 2% propane, 1% butanes, and 1% pentanes. The composition of the recycle gas is controlled such that the combined feed gas has the right composition to be ideal for the Liquid Fuel Production process using the preferred LFP catalyst. The LFP reactor feed (stream 14) has an approximate molar composition of 26% hydrogen, 13% CO, 19% methane, 1% propane, 1% butanes, 1% pentanes, and 38% carbon dioxide and 1% water and a flowrate of about 22,277 MT/D. The $H_2$/CO ratio of the LFP feed is 2.0. Through indirect heat exchange the temperature of the LFP feed is raised to 380° F. at a pressure of 330 psig. In certain cases: the LFP reactors are 10 reactors operating in parallel; the reactors are 30 meters tall from tangent to tangent; each reactor is comprising a shell with 5000 tubes inside; the tubes are approximately 19 mm outer diameter.

The syngas to hydrocarbon production reaction is exothermic. Steam is used outside of the LFP reactor tubes to control the temperature. The LFP reactors therefore raise steam that can be used to generate electricity. The LFP steam is used to generate 8.7 MW of electricity.

The preferred LFP reactor operating temperature is 410° F.

In certain cases: the LFP catalyst is a quadralobe catalyst with a mean particle radius of 50 micrometers and a pore diameter of 9 nm and a surface area of 140 $m^2$/g; the active metal is cobalt with a platinum or palladium promoter.

The catalyst particle diameter and the catalyst loading and the velocity of the LFP feed to the LFP reactor tubes are all managed such that the pressure drop across the LFP reactor tubes and reactors are minimized. In this example, the pressure drop is maintained at 20 psig.

The CO conversion in the LFP reactors is 55 mol %. The carbon selectivity to C5-C24 is 73.5% where carbon selectivity is defined as:

$$C5 - C24 \text{ Carbon Selectivity} = \frac{1}{n_{CO\ Converted}} \sum_{i=4}^{24} in_i$$

Where $n_{co}$ converted is the molar flowrate of CO that was converted in the LFP reactor; $n_i$ is the molar flowrate of $i^{th}$ carbon numbered hydrocarbon that was created in the LFP reactor. The carbon selectivity to carbon dioxide is low at 0.38% indicating that very little of the CO that was converted in the LF reactor was converted to carbon dioxide.

$$CO_2 \text{ Carbon Selectivity} = \frac{1}{n_{CO\ Converted}} n_{CO_2}$$

Where $n_{co2}$ is the molar flowrate of $CO_2$ that was created in the LFP reactor. This is highly desirable for the zero carbon fuels and chemical production process that starts with carbon dioxide as a feedstock.

The products proceed from the bottom of the reactor. There is the possibility that heavy hydrocarbons (C24+) are produced so the reactor exit can withdraw those products. If the LFP reactor is operated at the right conditions with the catalyst, there will be little or no heavy products. The primary LFP products are stream 16. The LFP product is further cooled to 333 F in step 17 and becomes stream number 24 that leaves FIG. 2.

The LFP product stream is cooled, products are condensed and then the LFP products are separated into three streams through separators in step 17. Product water (stream 26) that is produced from the LFP process is recycled to the electrolyzer and may require clean up or pre-treatment. The light gaseous products of the LFP reactor end up in streams 13 and 18 which are recycled to the feed of the LFP reactor and to the ATR. Optionally before this stream is recycled it may be additionally separated into two streams via a $CO_2$ separation system. The $CO_2$ rich stream may be recycled back to the RWGS reactor feed. The CO, $H_2$, and light hydrocarbons remaining in this stream are recycled back to the ATR.

The LFP product that comprises the C4-C24 hydrocarbon streams is separated into two streams to a gasoline blending stock and a diesel fuel. The products may also be further processed.

The example process has produced 1669 barrels per day (BPD) of naphtha/gasoline blendstock and 3387 BPD of diesel fuel. The LFP products may be further fractionated and processed to produce specialty chemicals including solvents, n-paraffins, olefins, and others.

Table 1 summarizes the Inputs for the Example. MT C/Day is the metric tons per day of carbon in that input. MT H/Day is the metric tons of hydrogen in the input. These are important for the carbon and hydrogen yield calculations.

TABLE 1

| | Example Inputs | | | |
|---|---|---|---|---|
| Inlets | MT/Day | MW | MT C/day | MT H/day |
| $CO_2$ | 1915 | | 522.3 | 0 |
| Water (Fresh) | 1212 | | 0 | 134.7 |
| Electricity | | 721.5 | | |

Table 2 summarizes the outputs for the Example.

TABLE 2

| | Example Outputs | | | |
|---|---|---|---|---|
| Outlets | BPD | MT/Day | MT C/day | MT H/day |
| Gasoline Blend Stock | 1669 | 181 | 154.4 | 26.8 |
| Diesel Fuel | 3387 | 412 | 350.9 | 60.8 |
| Total Products | 5056 | 593 | 505.3 | 87.6 |

Table 3 calculates some useful metrics for the example process.

TABLE 3

| Example Yield Metrics | | |
|---|---|---|
| Electricity Fuel Yield | 3.42 | MWh/Bbl. |
| Carbon Yield | 96.8% | carbon in product from $CO_2$ feed |

The example process and all processes of the invention will have carbon yields of greater than 70% and preferably greater than 85%. The overall process integration as well as the use of the disclosed RWGS catalyst and disclosed LFP catalyst are required to get carbon yields this high.

The invention claimed is:

1. An integrated process for the conversion of a feed stream comprising carbon dioxide to a product stream comprising hydrocarbons, the process comprising:
   a. an electrolysis step where an electrolyzer feed stream comprising water is converted to an electrolyzer product stream comprising hydrogen and oxygen, where electricity is used in the electrolysis step, and where at least a portion of the electricity used in the electrolysis step is from renewable or low carbon sources;
   b. a reverse water gas shift step where at least a portion of the hydrogen from the electrolyzer product stream is mixed with carbon dioxide to form a reverse water gas shift feedstock stream, and wherein the reverse gas shift feedstock stream is heated to a temperature greater than 1400° F., and where the electricity used in a radiant furnace to heat the reverse water gas shift feedstock stream is less than 0.5 MWh electricity/metric ton, and where the hydrogen from the reverse water gas feedstock stream is reacted with the carbon dioxide of the reverse water gas feedstock stream to produce a reverse water gas shift product stream comprising carbon monoxide, and where there is a per pass conversion of carbon dioxide to carbon monoxide when the carbon dioxide is reacted with the hydrogen in the reverse water gas shift reaction, and wherein the per pass conversion is between 30 and 90 mole %;
   c. a hydrocarbon synthesis step where at least a portion of the hydrogen from the electrolyzer product stream is reacted with a stream comprising at least a portion of the reverse water gas shift product stream to produce a hydrocarbon synthesis product stream comprising hydrocarbons, where there is a per pass conversion of carbon monoxide to the hydrocarbons, and where the per pass conversion is between 30 to 80 mole % carbon monoxide per pass.

2. The integrated process of claim 1 wherein the reverse water gas shift product stream is cooled, compressed, and fed into the liquid fuels production system.

3. The integrated process of claim 2 wherein the liquid fuels production system converts the reverse water gas shift product gas into hydrocarbon products where more than 50 percent of the products are C5 to C24 hydrocarbons.

4. The integrated process of claim 3 wherein the pressure of the reverse water gas shift step and the pressure of the liquid fuels production step are within 200 psi of each other.

5. The integrated process of claim 4 wherein the liquid fuels production system converts the blended products into hydrocarbon products, where more than 50 percent of the products are C4 to C24 hydrocarbons.

6. The integrated process of claim 1 wherein the source that the carbon dioxide is captured from is an industrial manufacturing plant that produces ammonia for fertilizer.

7. The integrated process of claim 1 wherein the source that the carbon dioxide is captured from is a cement plant.

8. The integrated process of claim 1 wherein the source that the carbon dioxide is captured from is an ethanol plant.

9. The integrated process of claim 1 wherein the source that the carbon dioxide is captured from is a petroleum refining plant.

10. The integrated process of claim 1 wherein the source that the carbon dioxide is captured from is a chemical plant.

11. The integrated process of claim 1 wherein the source that the carbon dioxide is captured from is a power plant that generates electricity.

12. The integrated process of claim 1 wherein the source that the carbon dioxide is captured from anaerobic digestion.

13. The integrated process of claim 1 wherein the source that the carbon dioxide is captured from the atmosphere.

14. The integrated process of claim 1 wherein the electrolyzer used for the electrolysis system operates using alkaline electrolysis.

15. The integrated process of claim 1 wherein the electrolyzer used for the electrolysis system operates using membrane electrolysis.

16. The integrated process of claim 1 wherein the electrolyzer used for the electrolysis system operates using high temperature electrolysis.

17. The integrated process of claim 1 wherein the electrolyzer has an electricity energy usage less than 60 MWh/MT of hydrogen produced.

18. The process of claim 1 wherein the electricity use in the RWGS radiant furnace is less than 0.20 MWh electricity/metric ton (MT) of CO2 in the RWGS feed gas and wherein the electricity is derived from a renewable source that comprises wind, solar, or geothermal, and wherein the CO2 conversion in the RWGS reactor is between 60 and 90% and the RWGS catalyst is a solid solution catalyst and the RWGS reactor weight hourly space velocity is between 1000 $hr^{-1}$ and 50,000 $hr^{-1}$.

19. The process of claim 5, where the hydrocarbon synthesis feedstock has a molar hydrogen to carbon monoxide ratio between 1.90 and 2.20 and the hydrocarbon synthesis catalyst comprises cobalt and the C4-C24 selectivity is greater than 70% and where the amount of carbon monoxide converted to products heavier than C24 is less than 10% and wherein the hydrocarbon produced has a lifecycle Green House Emissions reduction of 10% or more compared to the lifecycle Green House Emissions of petroleum products.

* * * * *